United States Patent [19]

Fatton

[11] 4,187,671
[45] Feb. 12, 1980

[54] ELECTRONIC WATCH WITH REACTION TIMER

[75] Inventor: Jean-Claude Fatton, Le Landeron, Switzerland

[73] Assignee: Ebauches Electroniques S.A., Marin, Switzerland

[21] Appl. No.: 851,176

[22] Filed: Nov. 14, 1977

[30] Foreign Application Priority Data

Nov. 22, 1976 [CH] Switzerland .................. 14639/76

[51] Int. Cl.² ............................................. G04B 47/06
[52] U.S. Cl. .................................... 58/152 B; 58/57.5;
307/10 R; 128/745; 273/1 E
[58] Field of Search ............... 58/16 R, 16 D, 22.7,
58/22.9, 23 R, 23 A, 23 C, 50 R, 57, 57.5, 74,
145 R, 145 A, 152 R, 152 B, 152 E, 152 F, 152
G; 307/10 AT, 10 R; 35/22 R; 273/1 E, 1 T;
128/2 N, 745

[56] References Cited

U.S. PATENT DOCUMENTS

| | | | |
|---|---|---|---|
| 3,165,883 | 1/1965 | Nash | 58/145 R |
| 3,563,230 | 2/1971 | Gibbs | 128/745 |
| 3,745,761 | 7/1973 | Tsuruishi | 58/23 R |
| 3,933,354 | 1/1976 | Goldfarb | 273/1 E |
| 3,961,473 | 6/1976 | Hung | 58/145 D |
| 4,044,544 | 8/1977 | Yagi | 58/152 B |
| 4,060,242 | 11/1977 | Huang | 273/1 E |
| 4,093,870 | 6/1978 | Epstein | 307/10 R |

FOREIGN PATENT DOCUMENTS 2424830 12/1975 Fed. Rep. of Germany .
374594 2/1964 Switzerland .
1180950 2/1970 United Kingdom .

*Primary Examiner*—B. Dobeck
*Assistant Examiner*—William L. Feeney
*Attorney, Agent, or Firm*—Wender, Murase & White

[57] ABSTRACT

An electronic watch circuits for the measurement and the display of time and for measuring a reaction time, and which further includes circuits controlling the display of a signal determined by comparing the measured reaction time with a reference time.

6 Claims, 1 Drawing Figure

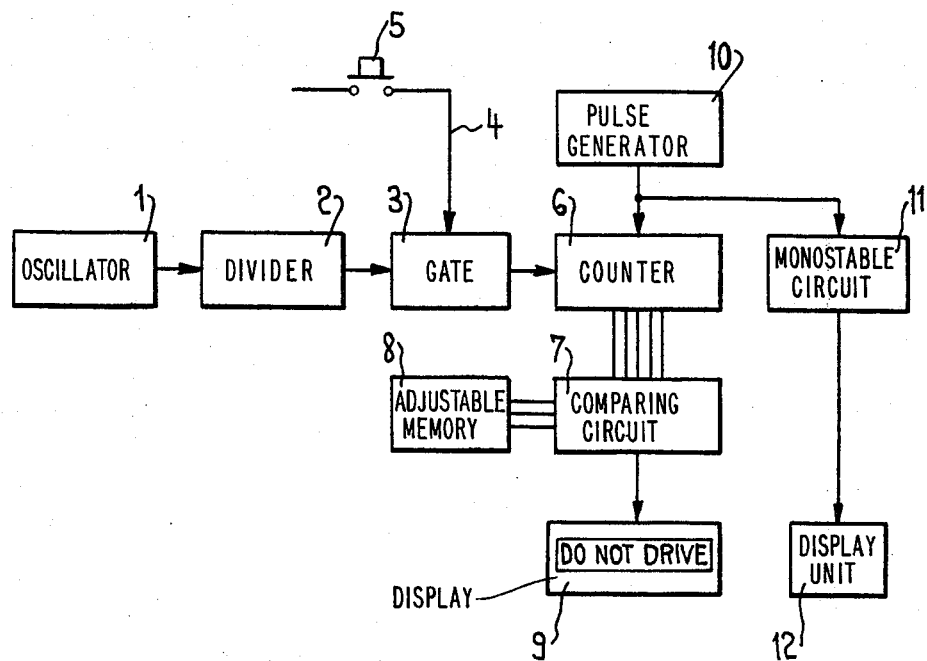

ELECTRONIC WATCH WITH REACTION TIMER

SUMMARY OF THE INVENTION

The present invention refers to an electronic watch including circuits for time measurement and display, and for measuring a reaction time, futher including circuits controlling the display of a signal determined by comparing the measured reaction time with a reference time.

The watch enables a vehicle driver to measure his time of reaction or reflex and thereby assess his capacity for driving the vehicle. The display of the watch can advantageously comprise means for displaying words like "DO NOT DRIVE", giving automatically and directly an answer to the question whether the attentiveness of the person conducting the test is sufficient for driving a vehicle or not.

In the following the invention is described more in detail with the aid of an embodiment represented as an example in the FIGURE.

DESCRIPTION OF THE PREFERRED EMBODIMENT

The watch as shown in the FIGURE comprises an oscillator 1 and a divider 2 for suitably dividing the frequency of oscillator 1 to provide clock signals for enabling the display of time and other watch functions. A suitable frequency, e.g. 128 Hz is delivered by divider 2 and fed to a gate circuit 3 enabled by its control circuit 4, which is controlled by push-button 5. The output of circuit 3 is connected to the input of a counter 6, which can take the form of a divider. The outputs of counter 6 are connected to inputs of a comparing circuit 7 for comparing the state of counter 6 to that of an adjustable memory 8. The comparing circuit 7 controls a display 9.

The watch comprises also a low frequency pulse generator 10, e.g. an astable multivibrator oscillating at a frequency of 0.2 Hz. The output of this pulse generator 10 controls on one hand the counter 6 by resetting it to zero by every pulse delivered by the pulse generator. On the other hand, the output of generator 10 controls a monostable circuit 11, which itself controls a display or signalling unit 12 generating a luminous or acoustical signal for every pulse coming from generator 10.

The watch can also comprise a supply circuit for the circuits 3 and 6 through 12 for activating these circuits only when the bearer of the watch intends to check his capacity or attentiveness.

When the circuits 3 and 6 through 12 are activated, the generator 10 generates pulses at intervals of 5 second, so that a luminous or acoustic signal is produced at 5 second intervals by the display or signalling unit 12. The counter 6 is reset to zero by every pulse of generator 10. During the interval between these pulses the output signal of divider 2 transmitted to counter 6 by the gate circuit 3 advances it to a determined state; then it is reset by the next pulse coming from the generator 10. Every time that the counter 6 exceeds a counting state corresponding to a state stored in the memory 8, the comparing circuit 7 transmits a signal to the display 9, which is activated until counter 6 is reset.

The bearer of the watch presses the push-button 5 as fast as possible after the appearance of a signal on the display unit 12; at this instant the passage of the signal of divider 2 to counter 6 is interrupted in the gate circuit 3 and counter 6 stops in a state depending on the reaction time between the appearance of the signal on the display unit 12 and the activating of the control circuit 4 by push-button 5. Depending whether the state attained by counter 6 is at least equal to the state stored in the memory 8 or not, the output of the comparison circuit 7 and the display 9 are activated or not. When the counting state of counter 6 passes the stored state, that is the reaction time is too long, the display 9 is activated and indicates to the bearer of the watch by the words "DO NOT DRIVE" that he should not drive a vehicle. After 5 seconds the counter 6 is reset by the next pulse of the generator 10 and the display 9 is extinguished if it had been activated. A circuit not shown can be provided for transmitting the information of the output of the comparison circuit 7 to the display 9 when the push-button is activated, and for storing this information until the next pulse of generator 10 is received. When push-button 5 is released, the circuits take up their initial functions described above and the bearer of the watch can repeat the test of his reaction time. The push-button 5 and the switch controlled by it can control another function of the watch, e.g. the lighting of the time display.

Because the signals are periodically generated at 5 second intervals, it is practically impossible to learn the cycle of the signal and to improve thereby the test result. However, it is possible to provide a pulse generator 10 delivering pulses at intervals more or less at random.

What I claim is:

1. An electronic watch capable of measuring the time in which a user of the watch reacts to a stimulus the occurrence of which is unknown to and independent of control of the user, comprising:
    oscillator means for generating clock signals;
    first display means providing the stimulus to signal the start of a reaction time test sequence;
    generator means coupled to said first display means for automatically activating said first display means independent of external control;
    counter means for counting said clock signals, said counter means being reset by said generator means simultaneous to actuation of said first display means;
    control means operatively coupled to said counter means for stopping the count thereof, said control means being manually operable by the user of the watch in response to the actuation of said first display means such that the count of said counter means is a measure of the reaction time of the user;
    means for memorizing a time reference;
    comparator means for comparing the reaction time represented by the count of said counter means with said memorized time of reference; and
    second display means controlled by the output of said comparator for delivering a warning whenever the reaction time exceeds said time of reference.

2. An electronic watch according to claim 1, wherein said generator means comprises a low frequency pulse generator and a monostable circuit, said monostable circuit coupling the output of said pulse generator to said first display means.

3. An electronic watch according to claim 1, wherein said memorizing means is adjustable to change the time of reference.

4. An electronic watch according to claim 1, wherein said control means comprises a gate connected between an output of said oscillator means and an input of said counter means.

5. An electronic watch according to claim 1, wherein said first display means delivers a luminous signal when actuated by said generator means.

6. An electronic watch according to claim 1, wherein said first display means delivers an acoustic signal when actuated by said generator means.

* * * * *